(12) United States Patent
Poisson et al.

(10) Patent No.: US 7,758,553 B2
(45) Date of Patent: Jul. 20, 2010

(54) DROP DISPENSER FOR THE DELIVERY OF UNIFORM DROPLETS OF VISCOUS LIQUIDS

(75) Inventors: Patrick Poisson, Boise, ID (US); Lyle M. Bowman, Pleasanton, CA (US)

(73) Assignees: Insight Vision Incorporated, Alameda, CA (US); R.P. Scherer Technologies, Inc., Las Vegas, NV (US)

( * ) Notice: Subject to any disclaimer, the term of this patent is extended or adjusted under 35 U.S.C. 154(b) by 347 days.

(21) Appl. No.: 11/397,047

(22) Filed: Apr. 3, 2006

(65) Prior Publication Data
US 2007/0233021 A1    Oct. 4, 2007

(51) Int. Cl.
*A61M 35/00* (2006.01)
*B65D 37/00* (2006.01)

(52) U.S. Cl. .............. 604/295; 604/298; 222/212; 222/215; 222/420

(58) Field of Classification Search ........... 604/295; 222/420–421
See application file for complete search history.

(56) References Cited

U.S. PATENT DOCUMENTS

| | | | | |
|---|---|---|---|---|
| 1,313,987 A | * | 8/1919 | Henry | 222/420 |
| 1,654,888 A | * | 1/1928 | King | 601/13 |
| 1,731,816 A | * | 10/1929 | Garhart | 222/562 |
| 2,249,832 A | * | 7/1941 | Hubschman | 222/420 |
| 2,734,665 A | * | 2/1956 | Flamm | 222/207 |
| 2,798,644 A | * | 7/1957 | Root | 222/215 |
| 2,811,283 A | * | 10/1957 | Bowen | 222/109 |
| 3,179,301 A | * | 4/1965 | Lucht | 222/213 |
| 3,248,017 A | * | 4/1966 | Allen | 222/207 |
| 3,552,605 A | * | 1/1971 | Hein | 222/207 |
| 4,629,456 A | * | 12/1986 | Edwards | 604/300 |
| 4,927,062 A | * | 5/1990 | Walsh | 222/420 |
| 5,048,727 A | * | 9/1991 | Vlasich | 222/209 |
| 5,181,632 A | * | 1/1993 | Latter | 222/153.06 |
| 5,219,101 A | * | 6/1993 | Matkovich et al. | 222/189.06 |
| 5,249,711 A | * | 10/1993 | Filbert, Jr. | 222/189.06 |
| 5,358,151 A | * | 10/1994 | Strasenburgh | 222/420 |
| 6,105,828 A | * | 8/2000 | Kanner et al. | 222/212 |

(Continued)

OTHER PUBLICATIONS

Declaration of Lyle M. Bowman; dated May 23, 2006 including Exhibits A and B.

(Continued)

*Primary Examiner*—Tatyana Zalukaeva
*Assistant Examiner*—Paula L Craig
(74) *Attorney, Agent, or Firm*—McDermott Will & Emery LLP

(57) ABSTRACT

A drop dispenser has a substantially conical sleeve member with a narrow upper end and a wide lower end. Centrally located at the apex of the upper end of the sleeve member is an aperture which has an inner diameter and is circumscribed by a raised ridge. The aperture and the ridge form a nozzle. The interior space of the substantially conical sleeve member forms a substantially conical chamber between the narrow upper end and wide lower end of the sleeve member. The nozzle is in liquid communication with the chamber through the aperture. The drop dispenser may have external threads at the lower end of the sleeve member for engaging a cap having a protuberance centrally located at its internal top end for hermetically engaging the aperture of the nozzle when the cap fully engages the sleeve member.

8 Claims, 5 Drawing Sheets

U.S. PATENT DOCUMENTS

| | | | | |
|---|---|---|---|---|
| 6,129,248 | A * | 10/2000 | Hagele | 222/420 |
| 6,168,581 | B1 * | 1/2001 | Buehler | 604/295 |
| 6,197,008 | B1 * | 3/2001 | Hagele | 604/295 |
| 6,303,631 | B1 * | 10/2001 | Sugahara et al. | 514/312 |
| 6,569,443 | B1 * | 5/2003 | Dawson et al. | 424/433 |
| 6,632,202 | B1 * | 10/2003 | Hagele | 604/295 |
| 7,063,241 | B2 * | 6/2006 | Spada et al. | 222/420 |
| 7,325,708 | B2 * | 2/2008 | Barber | 222/420 |
| 2002/0084290 | A1 * | 7/2002 | Materna | 222/420 |
| 2003/0069232 | A1 * | 4/2003 | Chiou | 514/224.8 |
| 2004/0210203 | A1 * | 10/2004 | Kusu et al. | 604/295 |
| 2005/0274744 | A1 * | 12/2005 | Spada et al. | 222/240 |
| 2006/0116649 | A1 * | 6/2006 | Hagele | 604/295 |
| 2007/0233020 | A1 * | 10/2007 | Hearne | 604/295 |

OTHER PUBLICATIONS

International Search Report issued in International Patent Application No. PCT/US07/07627, mailed Sep. 4, 2008.

* cited by examiner

DROP DISPENSER FOR THE DELIVERY OF UNIFORM DROPLETS OF VISCOUS LIQUIDS

FIELD OF THE INVENTION

The present invention relates to drop dispensers, such as for dispensing liquid medicine. The present invention has particular applicability to dispensing liquids having a viscosity higher than water.

BACKGROUND OF THE INVENTION

Various drop dispensers have been proposed wherein a desired or measured amount of liquid is discharged through a nozzle of said drop dispensers mounted on the outlet of a container containing the liquid. While these drop dispensers have been generally satisfactory for their intended purpose, they are characterized by a certain disadvantage in that when the liquid is of a viscosity substantially higher than that of water, the droplets dispensed from these drop dispensers are not of uniform size or are too large in volume because the drop forms on the surface area of the tip. Moreover, dispensers using a narrow passage between the liquid reservoir and the aperture where drops are formed are prone to entrap air bubbles in the stream of liquid to be dispensed, particularly when the liquid is viscous, preventing uniform formation and delivery of drops of liquid. Apparatuses prone to entrap air in the stream of liquid to be dispensed are thus rendered unsuitable for the convenient delivery of accurate volumes of liquid, such as is necessary for the deliver of medicament dosages. Therefore, it is necessary and desirable to develop a dispenser suitable for the convenient delivery of uniform amounts of liquids in drop format, such as for the delivery of medicaments formulations, even where the liquids are substantially more viscous than water.

SUMMARY OF THE INVENTION

The drop dispenser of the present invention permits dispensation of liquid droplets of uniform size, minimal volume and avoids the inclusion of air bubbles in the stream of liquid to be delivered, even where the liquid is substantially more viscous than water. The dispenser also avoids "ribboning" that can be observed with viscous materials that do not cleanly release from their ordinary dispensers to form droplets due to surface tension and viscoelastic properties of the liquid to be dispensed, and which leads to inconsistent delivery volumes. These characteristics make the presently claimed drop dispenser particularly useful where the convenient and consistent delivery of desired volumes of liquid are required, as in application medicaments, such as eye drops.

A drop dispenser for viscous liquids according to one aspect of the present invention comprises a substantially conical sleeve member having an upper end, a lower end that is wider than the upper end, and an aperture centrally located at the apex of the upper end. The aperture has an inner diameter and is circumscribed by a raised ridge having an outer diameter and a thickness, the aperture and raised ridge forming a nozzle at the upper end of the sleeve member. The interior space of the substantially conical sleeve member forms a substantially conical chamber between the upper end and the lower end, and the nozzle is in liquid communication with the chamber by way of the aperture.

In another aspect of the present invention, the lower end of the sleeve member has an external thread for engaging a cap, the cap having a protuberance centrally located at its internal top end that hermetically engages the nozzle when the cap is engaged. A breakaway cover encompasses the cap, and the lower end of the sleeve member comprises means for engaging a container. The container can be one of a squeezable bottle, a squeezable vial, a squeezable tube and a syringe, and made from a resilient material.

DETAILED DESCRIPTION OF THE INVENTION

The present invention provides a drop dispenser for the accurate, reproducible and convenient delivery of flowable liquids. In particular, the present invention provides a drop dispenser for delivering relatively small drops of viscous liquid. Standard conventional drop dispensers typically form drops of liquid solutions of about 30-50 microliters. However, when dispensing viscous liquids, they form much larger drops of about 40-75 microliters. In contrast, the dispenser of the present invention delivers drops of viscous liquids of about 25-40 microliters.

The drop dispenser of the present invention functions with a diversity of liquids including solutions, suspensions, and emulsions over a broad viscosity range. The inventive drop dispensing apparatus is capable of delivering accurate reproducible droplets of liquids having a viscosity substantially higher than water and up to about 15,000 centipoises.

The drop dispenser of the present invention comprises a substantially conical sleeve member that has an upper end, and a lower end that is wider than the upper end. Centrally located at the apex of the upper end of the sleeve member is an aperture which has an inner diameter and is circumscribed by a raised ridge. The ridge has an outer diameter and a thickness. The aperture and the ridge forms a nozzle. The interior space of the substantially conical sleeve member forms a substantially conical chamber between the narrow upper end and wide lower end of the sleeve member. The nozzle is in liquid communication with the chamber through the aperture.

In one embodiment, the drop dispenser of the present invention has at the lower end of the sleeve member external threads for engaging a cap. The cap has a protuberance centrally located at its internal top end that hermetically engages the aperture of the nozzle when the cap, through threads at its lower end, fully engages the sleeve member.

In other embodiments of the present invention, the cap is encompassed by a break-away cover that acts as both a means to protect the cap and drop-dispenser from physical damage and from contamination by dust and other undesirable contaminating matter. Moreover, as the break-away cover further acts as a tamper resistant seal, the drop dispenser is particularly suitable for the delivery of medicament formulations, such as eye drops.

In further embodiments of the present invention, the lower end of the drop dispenser is engageable with a suitable liquid container, and is particularly suitable for use with squeezably activated containers that may be used to force liquid from the drop dispenser.

Figure 1:
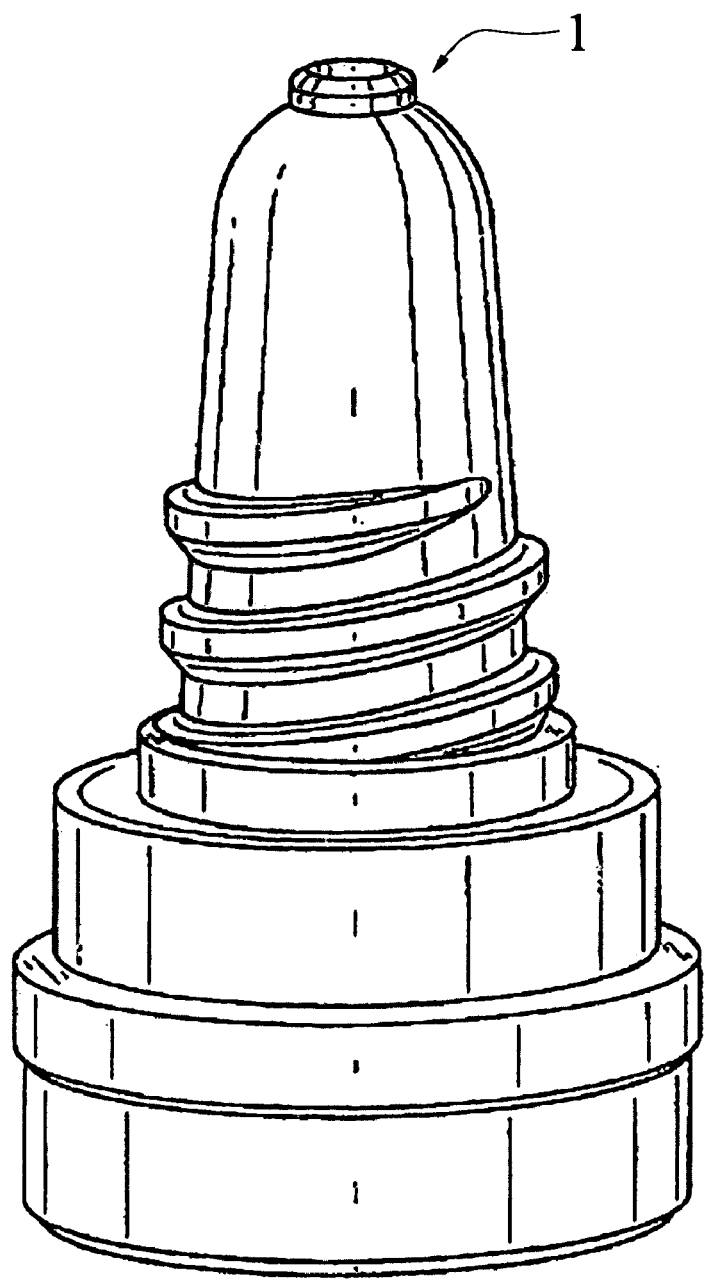
FIG. 1 is a perspective view of a drop dispenser according to an embodiment of the present invention.
Figure 2:
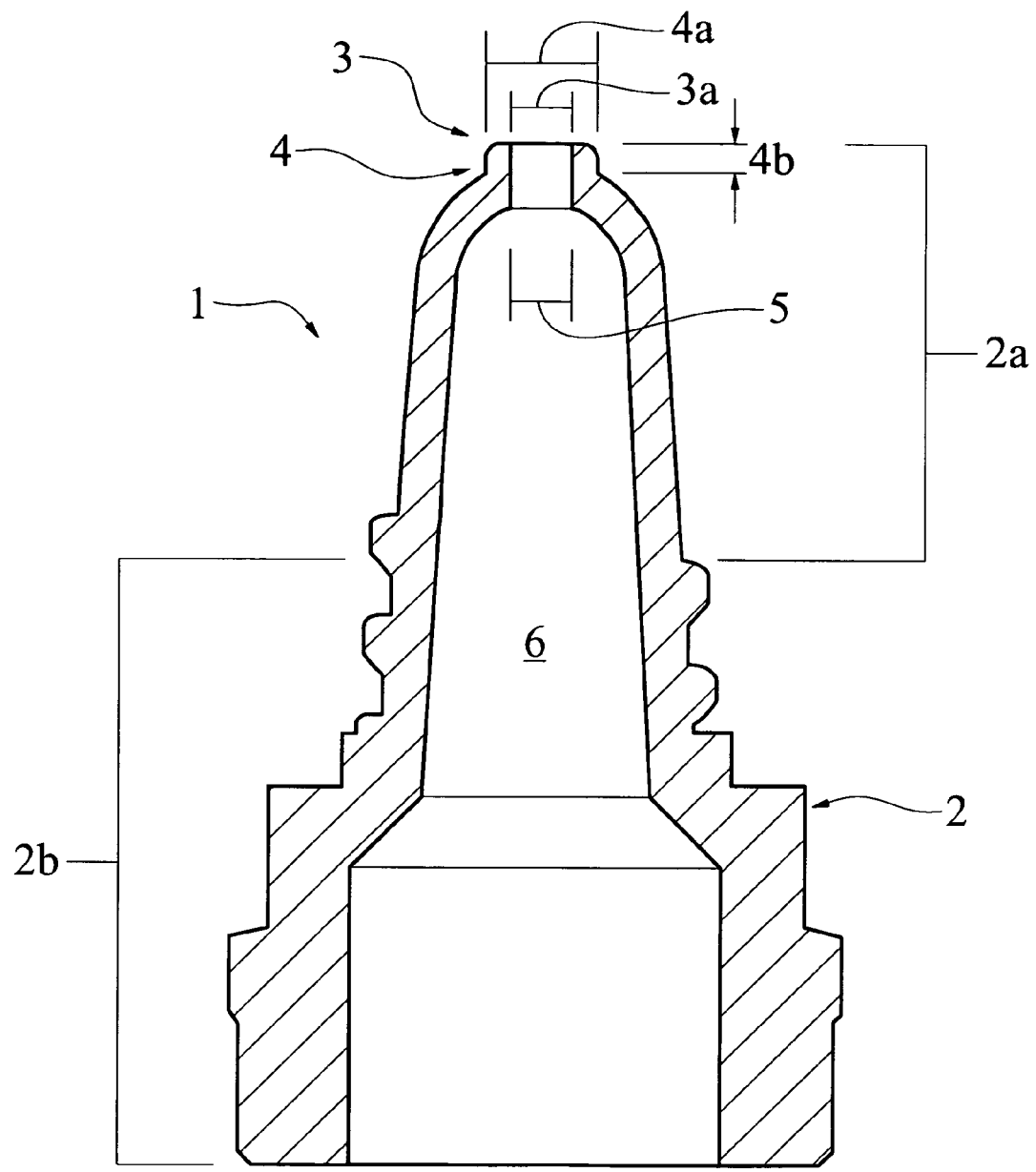
FIG. 2 is a side sectional view of the drop dispenser of FIG. 1.
Figure 3:
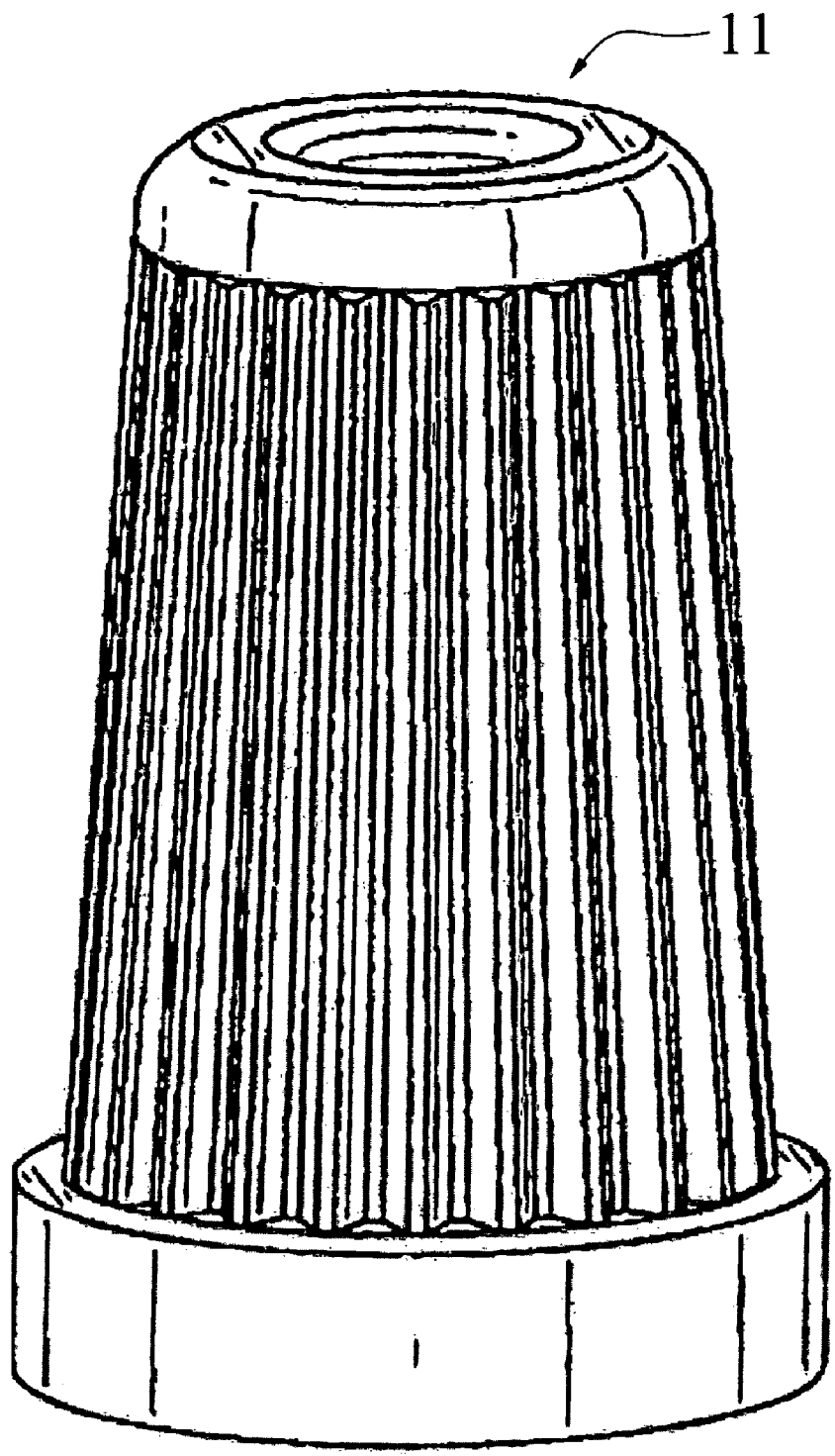
FIG. 3 is a perspective view of a cap usable with the drop dispenser of FIG. 1.
Figure 4:
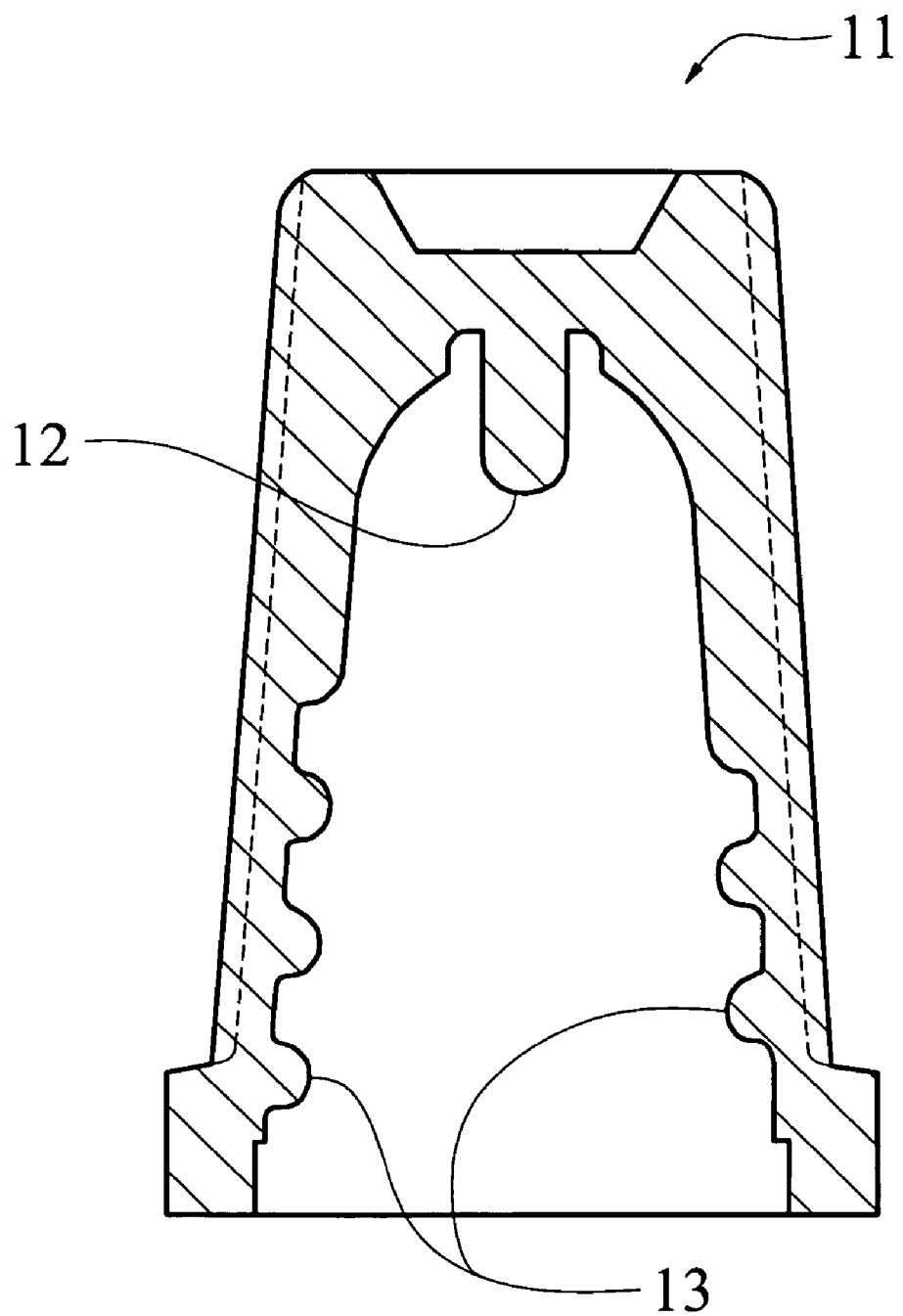
FIG. 4 is a side sectional view of the cap of FIG. 3.
Figure 5:
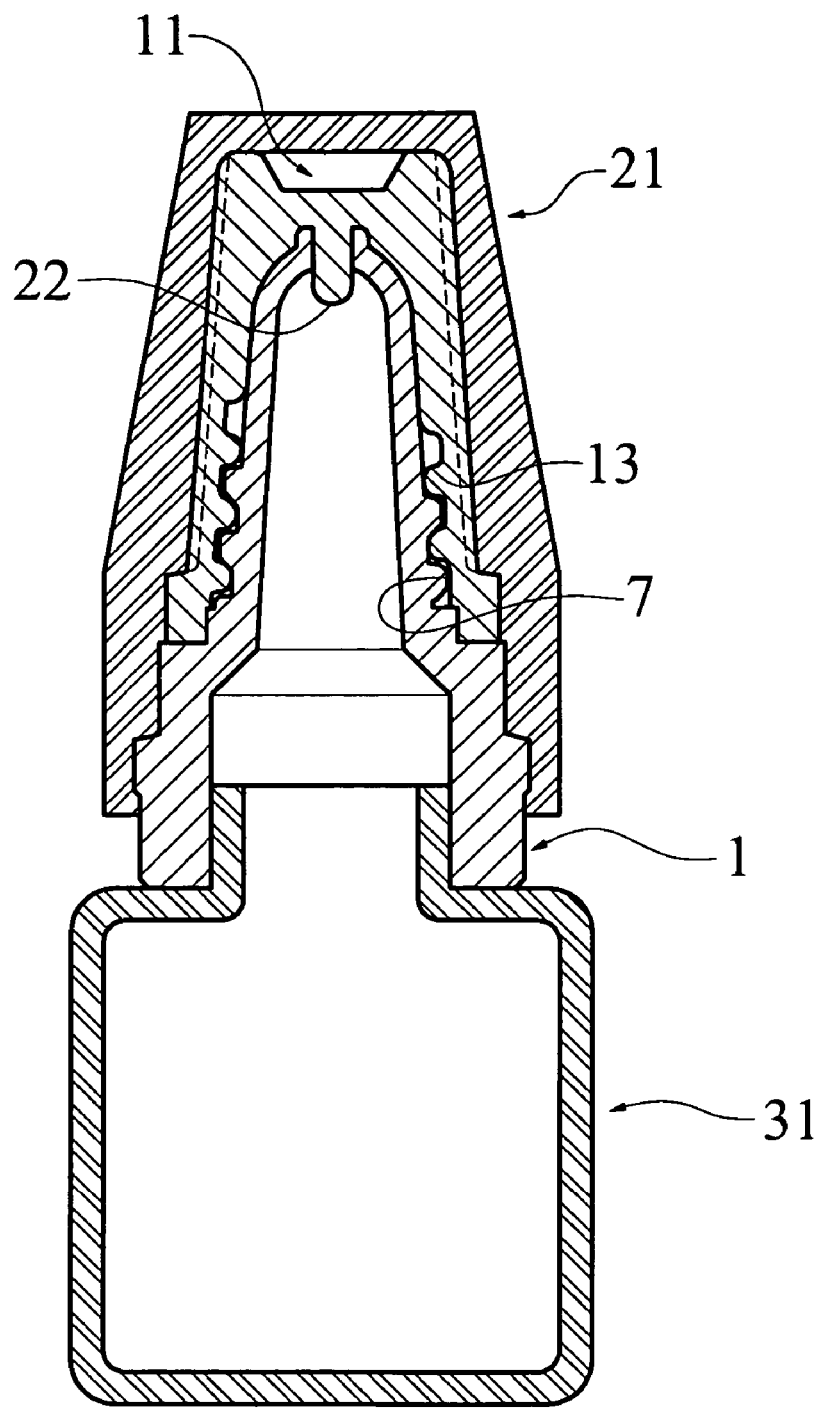
FIG. 5 is a partial sectional view of a drop dispenser according to the present invention mounted on a container, with a cap fully engaged and an optional break-away cover.

Embodiments of the present invention will now be described in detail with reference to FIGS. 1-5. A drop dispenser (1) of the present invention, as shown in FIGS. 1, 2 and 5, comprises a substantially conical sleeve member (2) that has an upper end (2a) and a lower end (2b) wider than upper end (2a). Centrally located at the apex of the upper end (2a) is an aperture (3) which has an inner diameter (3a) and is circumscribed by a raised ridge (4). The ridge has an outer diameter (4a) and a thickness (4b). The aperture (3) and the ridge (4) form a nozzle (5), which has the same outer diameter as the ridge (4) that forms it. The interior space of the substantially conical sleeve member (2) forms a substantially conical chamber (6) between the narrow upper end (2a) and wide lower end (2b) of the sleeve member (2). The nozzle (5) is in liquid communication with the chamber (6) through the aperture (3).

The inner diameter (3a) and outer diameter (4a) are measured across the center of the aperture and the ridge. The thickness (4b) of the ridge (4) is measured perpendicular to the top surface of the ridge (4) from the top surface of the ridge (4) along the perpendicular outer surface of the ridge (4) to the point where the ridge (4) meets the convex surface of the upper end (2a) of the sleeve member (2). In one embodiment, the inner diameter (3a) of the aperture (3) is from about 0.010 to about 0.060 inches, the outer diameter (4a) of the ridge (4) and nozzle (3) is the inner diameter (3a) of the aperture (3) plus from about 0.020 to about 0.060 inches, and the thickness (4b) of the ridge (4) is from about 0.005 to about 0.040 inches.

In another embodiment, the inner diameter (3a) of the aperture is from about 0.030 to about 0.070 inches, and the outer diameter (4a) is the inner diameter (3a) plus from about 0.030 to about 0.050 inches, and the thickness (4b) of the ridge is from about 0.008 to about 0.020 inches. In a further embodiment, the inner diameter (3a) of the aperture is about 0.050 inches, the outer diameter (4a) is the inner diameter (3a) plus about 0.040 inches, and the thickness (4b) of the ridge is about 0.010 inches. In a still further embodiment, the inner diameter (3a) of the aperture is about 0.050 inches, the outer diameter (4a) is about 0.090 inches, and thickness (4b) of the ridge is about 0.025 inches.

The substantially conical chamber (6) has a volume that is substantially greater than the volume of the drop formed from the drop dispenser. In one embodiment, the chamber (6) has a volume that is at least 5 times the volume of the drop formed from the drop dispenser. In another embodiment, the chamber (6) has a volume that is at least about 125 microliters. In a further embodiment the chamber (6) has a volume of at least about 500 microliters. In still another embodiment the chamber (6) has a volume of at least about 1,000 microliters. In some embodiments, chamber (6) volume is from 125 microliters to about 1,500 microliters; in other embodiments from about 500 microliters to about 1,000 microliters; and in still other embodiments from about 500 microliters to about 1,500 microliters.

In one embodiment, the drop dispenser of the present invention has, at the lower end (2b) of the sleeve member (2), external threads (7) for engaging a cap (11). The cap (11), as shown in FIGS. 3-5, has a protuberance (22) centrally located at its internal top end that hermetically engages the aperture (3) of the nozzle (5) when the cap (11), through threads (13) at its lower end, fully engages the sleeve member (2).

Use of the inventive cap (11) is optional; a conventional cap can be used in its place. If such a standard cap is used, the seal should be made at the threads (7), and the cap must be sized to ensure it does not contact the aperture (3) of the nozzle (5), to avoid damaging the nozzle (5).

In certain embodiments, the cap (11) is encompassed by a conventional break-away cover (21), as shown in FIG. 5, that acts as both a means to protect the cap and the drop-forming end (i.e., nipple) of the drop dispenser from contamination by unwanted materials such as dust. In addition, the break-away cover (21) can act as a tamper proof seal, making the package particularly useful for applications were it is desirable to determine if the contents have been tampered with, used or possibly contaminated by use, as is the case where the dropper is used for the delivery of medicaments. Moreover, because the break-away cover (21) shields the cap (11) and drop-dispensing end (1) from the environment, it aids in maintaining the cap and drop-forming end of the dispenser sterile where contents have been so packaged.

In one embodiment, the drop dispenser of the present invention further comprises a means for engaging a container (31) at the lower end (2b) of the sleeve member (2), as shown in FIG. 5. Such means include, but are not limited to, threads that threadably connect with cooperating threads at the container (31), insertion during form fill seal molding, snap-fit and/or press-fit means, thermal or ultrasonic welding means, a means for engaging a heat shrinkable container, O-ring seals, and compression fitting means.

In those embodiments providing for the presence of a container, the container (31) may be a squeezable bottle or a squeezable vial. In another embodiment, the container (31) is a squeezable tube. In still another embodiment, the container (31) is a syringe. One of ordinary skill in the art would appreciate that many other types of containers are readily adaptable to engage the drop dispenser of the present invention.

The drop dispenser (1), the cap (11), the break-away cover (21) and the container (31) that engages the drop dispenser can be made of a wide variety of suitable materials. In one embodiment, the drop dispenser (1), the cap (11), the break-away cover (21) and the container (31) are made of suitable, resilient materials. In another embodiment, the container (31) is made of suitable soft, resilient material. In other embodiments, the drop dispenser (1), the cap (11), the break-away cover (21) and the container (31) are made of the same or different materials selected from: high density polyethylene, low density polyethylene, and very low density polyethylene. One of ordinary skill in the art would appreciate that many other types of materials including but not limited to polypropylene, blended polypropylene-polyethylene copolymers, polyvinyl chloride ("PVC"), polyethylene terepthalate ("PET"), polytetrafluoroethylene ("Teflon®"), acrylonitrile-butadiene-styrene ("ABS"), polystyrene, polycarbonate, polyamides, and polyesters, are readily adaptable to be used for the drop dispenser (1), the cap (11), the break-away cover (21) or the container (31) of the present invention. The choice of materials employed in constructing the drop dispenser will depend on the material's compatibility with the liquid to be dispensed.

The liquids to be dispensed can take the form of a solution, a suspension, or an emulsion. In one embodiment, the liquid is aqueous or has water as the majority of the liquid present. In another embodiment, the liquid is an aqueous composition that has a viscosity substantially higher than that of water. In still another embodiment the formulation has a solvent other than water as a majority of the liquid present. Regardless of whether the liquid to be dispensed is an aqueous or non-aqueous composition, the drop dispenser is employable to dispense liquids with a viscosity from about 10 to about 15,000 centipoises. In one embodiment, the liquid to be dispensed has a viscosity from about 100 to about 10,000 centipoises; for example, about 500 to 5000 centipoises. In another embodiment, the liquid to be dispensed has a viscosity from about 100 to about 15,000 centipoises. In yet another embodiment, the liquid to be dispensed has a viscosity from about 1,000 to about 5,000 centipoises. In some embodiments, the liquid to be dispensed is a medicament. In another embodiment, the liquid to be dispensed is an ophthalmic formulation to be delivered as an eye drop.

The drop dispenser of the present invention allows for the delivery of liquid droplets devoid of air bubbles, even when the liquid has a viscosity that is substantially higher than that of water. Upon proper application, including but not limited to when the dispenser is held in a near-vertical orientation with the nozzle directed downward, the dispenser produces droplets of sufficient uniformity and volume to be used in the delivery of medicaments over the range of 10 to 15,000 centipoises. Where the drop dispenser is fitted to a squeezably activated container, it can be employed to dispense droplets by orienting the dispenser so that liquid fills the conical chamber, and gently squeezing the container. Those of ordinary skill in the art will appreciate that the consistent delivery of viscous liquid droplets that are small and uniform in size and devoid of air bubble so achieved offers a significant advantage for the application of, for example, viscous eye drops.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only an exemplary embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A drop dispenser for dispensing a viscous liquid, comprising a substantially conical sleeve member having an upper end, a lower end, and an aperture centrally located at the apex of the upper end;

wherein the lower end of the sleeve member is wider than the upper end of the sleeve member;

wherein the aperture has an inner diameter and is circumscribed by a raised ridge having an outer diameter, an inner diameter the same as the inner diameter of the aperture, and a thickness, the aperture and raised ridge forming a nozzle at the upper end of the sleeve member;

wherein the outer diameter of the raised ridge has a smaller diameter than an outer diameter of an upper surface of the upper end of the sleeve member;

the thickness of the ridge extends parallel to a longitudinal axis of the drop dispenser;

wherein the outer diameter of the raised ridge extends parallel to the inner diameter of the aperture along a portion of the thickness of the raised ridge;

wherein an interior space of the substantially conical sleeve member forms a substantially conical chamber between the upper end and the lower end, wherein the nozzle is in liquid communication with the chamber by way of the aperture; and wherein the inner diameter of the aperture is from about 0.010 to about 0.060 inches, the outer diameter of the raised ridge is the inner diameter plus about from 0.020 to about 0.060 inches, and the thickness of the entire ridge is from about 0.005 to about 0.040 inches;

the conical chamber has a volume that is at least 5 times the volume of a drop formed from the drop dispenser;

the conical chamber has a volume of from 500 microliters to about 1000 microliters;

the lower end of the sleeve member comprises means for engaging a container;

the container comprises a resilient material;

the container comprises one of a squeezable bottle, a squeezable vial, a squeezable tube, and a syringe;

the nozzle is dimensioned and configured for delivering drops of the viscous liquid with each drop having a volume of about 25-40 microliters, the viscous liquid having a viscosity from about 100 to about 10,000 centipoises.

2. The drop dispenser of claim 1, wherein the inner diameter of the aperture is about 0.050 inches.

3. The drop dispenser of claim 1, wherein the inner diameter of the aperture is about 0.050 inches, the outer diameter of the raised ridge is the inner diameter plus about 0.040 inches, and the thickness of the ridge is about 0.010 inches.

4. The drop dispenser of claim 1, wherein the lower end of the sleeve member has an external thread; further comprising a cap having an internal thread engageable with the external thread, and a protuberance centrally located at an internal top end for hermetically engaging the nozzle when the cap is engaged with the external thread.

5. The drop dispenser of claim 4, further comprising a breakaway cover encompassing the cap.

6. The drop dispenser of claim 1, wherein the drop dispenser comprises one of polypropylene, blended polypropylene-polyethylene copolymers, polyvinyl chloride ("PVC"), polyethylene terepthalate ("PET"), polytetrafluoroethylene, acrylonitrile-butadiene-styrene ("ABS"), polystyrene, polycarbonate, polyamides, and a polyester.

7. The drop dispenser of claim 1, wherein the viscous liquid has a viscosity from about 1,000 to about 5,000 centipoises.

8. The drop dispenser of claim 1, wherein the inner diameter of the aperture is about 0.050 inches, the outer diameter of the raised ridge is about 0.090 inches, and thickness of the ridge is about 0.025 inches.

* * * * *